United States Patent [19]
Sato et al.

[11] Patent Number: 6,136,600
[45] Date of Patent: Oct. 24, 2000

[54] METHOD FOR CULTIVATION OF HEPATOCYTES

[75] Inventors: Hajime Sato; Katsutoshi Yoshisato, both of Hiroshima, Japan

[73] Assignee: Japan Science and Technology Corporation, Saitama, Japan

[21] Appl. No.: 09/092,305

[22] Filed: Jun. 5, 1998

[30] Foreign Application Priority Data

Jun. 6, 1997 [JP] Japan ................................. 9-149708

[51] Int. Cl.$^7$ ....................................................... C12N 5/00
[52] U.S. Cl. ........................... 435/370; 435/383; 435/384; 435/404; 435/405

[58] Field of Search ................................ 435/383, 384, 435/404, 405, 370

Primary Examiner—Leon B. Lankford, Jr.
Attorney, Agent, or Firm—Wenderoth, Lind & Ponack, L.L.P.

[57] ABSTRACT

The present invention provides a method for cultivation of hepatocytes efficiently by using a hepatocyte growth promoting factor derived from 3T3 cells, which comprises culturing hepatocytes isolated from the liver of a matured mammal in a medium containing pleiotrophin, fetal bovine serum, ascorbic acid or analogues thereof and nicotinamide or an analogue thereof, thereby forming primary colonies of the hepatocytes; and a method for subculture of the primary hepatocytes in the same medium.

20 Claims, 3 Drawing Sheets

METHOD FOR CULTIVATION OF HEPATOCYTES

BACKGROUND OF THE INVENTION

1. Field of the Invention

The present invention relates to a method for cultivation of hepatocytes. More particularly, the present invention relates to a method of efficient primary culture and subculture of hepatocytes useful as materials for research in cell biology and molecular biology on development, differentiation and proliferation process of hepatocytes or on the carcinogenic mechanism thereof, or as medical materials for development of therapeutic techniques of various hepatic diseases.

2. Description of the Related Art

An animal is a multicellular organism formed through repeated division of a fertilized egg and differentiation thereof into various structures (collar aggregates) which take charge of different functions. Each structure composing a body of organisms maintains the individual by producing cells having active differentiation ability through constant division and growth of individual cells. Therefore, in order to understand the biological facts of animals including humans or to develop therapeutic techniques through elucidation of the carcinogenic mechanism, it is believed to be important to make a detailed analysis of cells constituting individual structures and to clarify the development and differentiation process and the mechanism of proliferation by techniques of cell biology or molecular biology.

Methods have been conventionally well established, as a means to analyze in detail cells of structures in vivo, to culture cells taken out in vitro, and further divide and grow the cultured cells to ensure survival through subcultures. However, subculture of primary hepatocytes isolated from matured individuals has been considered impossible if hepatocytes from rats and mice are used. That is, adhesion-dependent matured hepatocytes are seriously damaged upon detachment from a culture substrate in the operation of subculture and further these cells are difficult to adhere again onto a culture substrate, so it is not possible to study the development, differentiation and proliferation process of hepatocytes in the subculture system.

The present inventors have overcome such difficulty by developing ingredients and the like in a culture medium, thus succeeding in subculture of primary cells isolated from the liver of a matured rat, and this culture method has already been filed as a patent application (Japanese Patent Application No. 89056/1996).

Further, the present inventors have obtained parenchymal hepatocytes having a clonal growth ability considered to contain hepatic progenitor cells whose presence had not been confirmed at that time, a method of preparation thereof and a method of subculture thereof, and the present inventors have filed a patent application therefor (Japanese Patent Application No. 213686/1995).

Further, the present inventors have found that a small number of hepatocytes can be efficiently proliferated by adding a culture supernatant (conditioned medium: CM) of 3T3 cells to a culture medium for hepatocytes or by co-culturing hepatocytes with 3T3 cells, and these culture methods have been filed as a patent application (Japanese Patent Application No. 133985/1996).

SUMMARY OF THE INVENTION

Because a CM of 3T3 cells or co-culturing with 3T3 cells promotes growth of hepatocytes in the method of Japanese Patent Application No. 133985/1996 mentioned above, it is estimated that 3T3 cells produce a certain growth promoting factor for hepatocytes.

Accordingly, the object of the present invention is to provide an improved culture method for cultivation of hepatocytes efficiently by specifying a hepatocyte growth promoting factor produced by 3T3 cells and using this growth promoting factor.

As a result of their eager study for specifying a hepatocyte growth promoting factor produced by 3T3 cells, the present inventors found this factor to be pleiotrophin to arrive at the present invention.

That is, the first invention of the present application is a method for primary culture of hepatocytes comprising culturing hepatocytes isolated from the liver of a matured mammal containing pleiotrophin, fetal bovine serum and nicotinamide or an analogue thereof, thereby forming the primary colonies of the hepatocytes.

The second invention is a method for subculture of hepatocytes, which comprises:

(a) culturing hepatocytes isolated from the liver of a matured mammal in a medium containing fetal bovine serum and nicotinamide or an analogue thereof, thereby forming the primary colonies of the hepatocytes;

(b) detaching the colony cells from the medium by using a solution containing EDTA and trypsin to disperse the cells;

(c) re-culturing the dispersed hepatocytes in a medium containing pleiotrophin, fetal bovine serum and nicotinamide or an analogue thereof, thereby forming the secondary colonies of the hepatocytes; and (d) repeating the steps (b) and (c) to form multi-generated colonies of the hepatocytes.

The third invention is a method for subculture of hepatocytes, which comprises:

(a) culturing hepatocytes isolated from the liver of a matured mammal in a medium containing pleiotrophin, fetal bovine serum and nicotinamide or an analogue thereof, thereby forming colonies of the hepatocytes;

(b) detaching the colony cells from the medium by using an EDTA/trypsin solution to disperse the cells;

(c) re-culturing the dispersed hepatocytes in the same medium as in the stop (a), thereby forming the secondary colonies of the hepatocytes; and (d) repeating the steps (b) and (c) to form the multi-generated colonies of the hepatocytes.

In preferred embodiments of these methods, the medium further contains ascorbic acid or an analogue thereof, and the medium is DMEM medium containing epidermal growth factor and DMSO.

DESCRIPTION OF THE PREFERRED EMBODIMENTS

Figure 1:
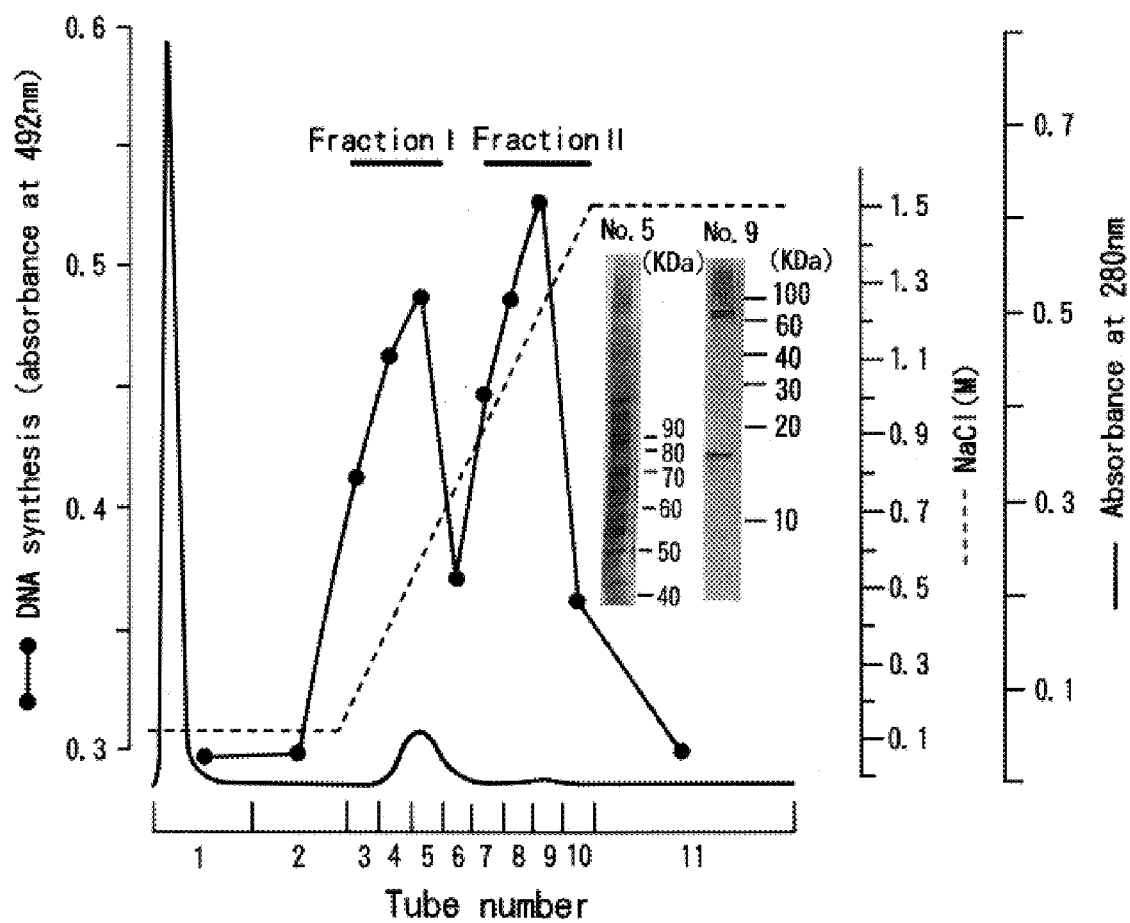
FIG. 1 shows the result of separation of 3T3 cell-derives growth promoting factors by a column of heparin-Sepharose. —:Absorbance at 280 nm; •—•:BrdU incorporated; . . . :NaCl concentration. The right space is proteins separated from tube 5 and 9 on SDS-PAGE.

Hepatocytes to be subjected to the primary culture in the first invention may be any cells constituting the liver of a matured mammal, and such cells can be isolated from the liver of an animal in a method known in the art, and then cells contained in a fraction precipitated by low-speed centrifugation (50 G) are cultured. For this culture, the first invention makes use of a medium to which pleiotrophin (PTN), fetal bovine serum (FBS) and nicotinamide or an analogue thereof have been added. More preferably, the medium further contains an ascorbic acid or an analogue thereof (e.g. L-ascorbic acid phosphate)

That is, while in one embodiment of the culture method in the above prior application (Japanese Patent Application No. 133985/1996), hepatocytes are cultured in a mixed medium consisting of a medium containing FBS and nicotinamide or an analogue thereof as colony-forming ingredients for hepatocytes and a CM of 3T3 cells as a growth promoting factor for hepatocytes, the method of the present invention is characterized in that PTN is added in place of a CM of 3T3 cells to the medium of said prior application.

The compound PTN is one of heparin-binding proteins, and its action as growth factor and trophic factor for nerve cells is known. Some researchers have reported its action of promoting division of somatic cells such as fibroblasts, endothelial cells, epithelial cells etc., but there are also reports negating such action, so the effect of PTN on somatic cells is not established (The Journal of Biological Chemistry, Vol. 267, No. 36, pp. 25889–25897, 1992). In particular, its physiological activity on hepatocytes has not been known up to now.

The compound PTN is commercially available as recombinant human PTN (R&D Systems Inc.), and this commercial product can also be used in the method of the present invention. Using the isolation and purification procedures described below, PTN can also be obtained from a CM of 3T3 cells prepared in the same manner as in the prior application (Japanese Patent Application No. 133985/1996) or from a culture supernatant of other animal cells. Alternatively, PTN derived from 3T3 cells may be obtained by using a part of a known amino acid sequence of PTN as a probe to isolate a coding sequence of PTN from an existing cDNA library and then expressing this coding sequence in a suitable host-vector system.

The medium to which PTN, FBS, ascorbic acid or an analogue thereof and nicotinamide or an analogue thereof are added as the essential ingredients is specifically DMEM medium containing epidermal growth factor and DMSO. The epidermal growth factor (EGF) and DMSO are not essential for colony formation but are preferably added to the medium by virtue of their action of promoting colony formation. A fraction obtained by low-speed centrifugation contains endothelial cells, Kupffer's stellate cells, stellate cells, bile-duct epithelial cells in addition to hepatocytes and is considered to provide hepatocytes with a specific environment, and said nicotinamide or an analogue thereof, ascorbic acid or an analogue thereof and DMSO inhibit the growth of these non-parenchymal cells, thus making it possible to selectively culturing and proliferating parenchymal hepatocytes. The amounts of these ingredients added to the medium can be, for example, about 0.1 ng/ml to 10 μg/ml for PTN, 5 to 30% for FBS, 0.1 to 1.0 mM for ascorbic acid or an analogue thereof, 1 to 100 ng/ml for EGF, 1 to 20 mM for nicotinamideor an analogue thereof, and 0.1 to 2% for DMSO. Culture is conducted in a 5% $CO_2$ atmosphere at a temperature of about 37° C.

The primary colonies of hepatocytes are obtained according to the culture as described above. Cells forming these colonies are further screened by the method of the prior application (Japanese Patent Application No. 133965/1996) whereby parenchymal hepatocytes and non-parenchymal cells can be identified.

Hereinafter, the method for subculture of hepatocytes according to the present invention (second and third inventions) is described.

These subculture methods involve detaching colonies of hepatocytes obtained in primary culture (primarily cultured cells) from a vessel and culturing them again in another vessel to proliferate the cells. The same method as in said prior application (Japanese Patent Application No. 213686/1995) may be used as the primary culture method (second invention), or the primary culture method according to the first invention may be used (third invention). To detach colonies of primarily cultured cells obtained in either method, the medium is removed from the vessel and then the colonies are treated with a solution of EDTA (0.002 to 0.2%) and trypsin (0.005 to 0.5%) for about 10 minutes whereby the colonies can be separated into hepatocytes and non-parenchymal cells. The liquid containing these separated cells is filtered through a filter (pore diameter: about 20 μm) to remove small aggregations so that the cells can be dispersed.

In the subculture methods of the present invention, the cells thus dispersed are cultured again in a medium to which PTN, FBS and nicotinamide or an analogue thereof have been added. More preferably, the medium is further added with an ascorbic acid or an analogue thereof. By this subculture, colonies can be efficiently formed even if the cells are inoculated at low cell density (for example, about $1 \times 10^4$ cells/35 mm dish). The specific ingredients in the medium may be the same as in the first invention.

The methods of this invention as described above can be applied to hepatocytes from every mammal including human, so the hepatocytes (parenchymal hepatocytes) having a clonal growth ability obtained from various animal species can be subjected to primary culture to form colonies and these primarily cultured cells can be further subcultured. The subcultured cells with a clonal growth ability from parenchymal hopatocytes recovered from human livers can be used to produce hydrid-type artificial liver etc., and are expected to bring about new developments in techniques for treatment of hepatic diseases as well.

As described above in detail, the present invention permits efficient colony formation of hepatocytes from a matured mammal and subsequent subculture thereof. Accordingly, the present invention enables detailed study on the development and differentiation process of hepatocytes and on the mechanism of proliferation and expression of functions thereof, thus providing a new means of elucidating the mechanism of human hepatic diseases including hepatoma as well as for developing therapeutic methods.

EXAMPLES

Hereinafter, the subculture method of this invention is described in more detail and specifically with reference to Examples, which however are not intended to limit the present invention.

Example 1

Preparation of PTN

3T3 cells inoculated onto a vessel ($5 \times 10^3$ cells/10 cm dish) were cultured in DMEM medium containing 10% FBS, penicillin and streptomycin until the cells became confluent. Then, the cells were washed twice with PBS, the medium was exchanged with FBS-free DMEM medium, and the cells were cultured at 37° C. in a 5% $CO_2$ atmosphere for 48 hours. This medium (3T3 CM) was filtered through a filter with a pore diameter of 0.45 μm and concentrated 50-fold through an ultramembrane.

Then, this concentrated 3T3 CM was fractionated through a heparin column. The heparin column was previously equilibrated with PBS buffer. The proteins adsorbed onto the column were eluted with NaCl The resulting fractions were sterilized by filtration through a filer with a pore diameter of 0.22 μm, and each fraction was added to DMEM medium (10% FBS, 44 mM $NaHCO_3$, 20 mM HEPES, 0.5 mg/l insulin, $10^{-7}$ M dexamethasone, 30 mg/l L-proline, penicillin, streptomycin, 10 mM nicotinamide, 10 ng/ml EGF and 0.2 mM L-ascorbic acid phosphate), and hepatocytes were cultured in it for 4 days. Then, BrdU was added to the medium, and after 48 hours, synthesis of DNA by the hepatocytes was determined by examining their incorporation of BrdU in ELISA. As a result, as shown in FIG. 1, the mitogenic activity was separated into two fractions: fraction I (tube number 3 to 5) eluted with NaCl from 0.2 M to 0–0.6 M and fraction II (tube number 7 to 10) eluted with NaCl from 0.8 M to 1.4 M. That is, the incorporation or BrdU into the hepatocytes was raised when a fraction eluted with at least 0.8 M NaCl was added to the medium so that the promotion of DNA synthesis was confirmed, and it was thus revealed that a hepatocyto growth promoting factor was present in this fraction.

Figure 2:
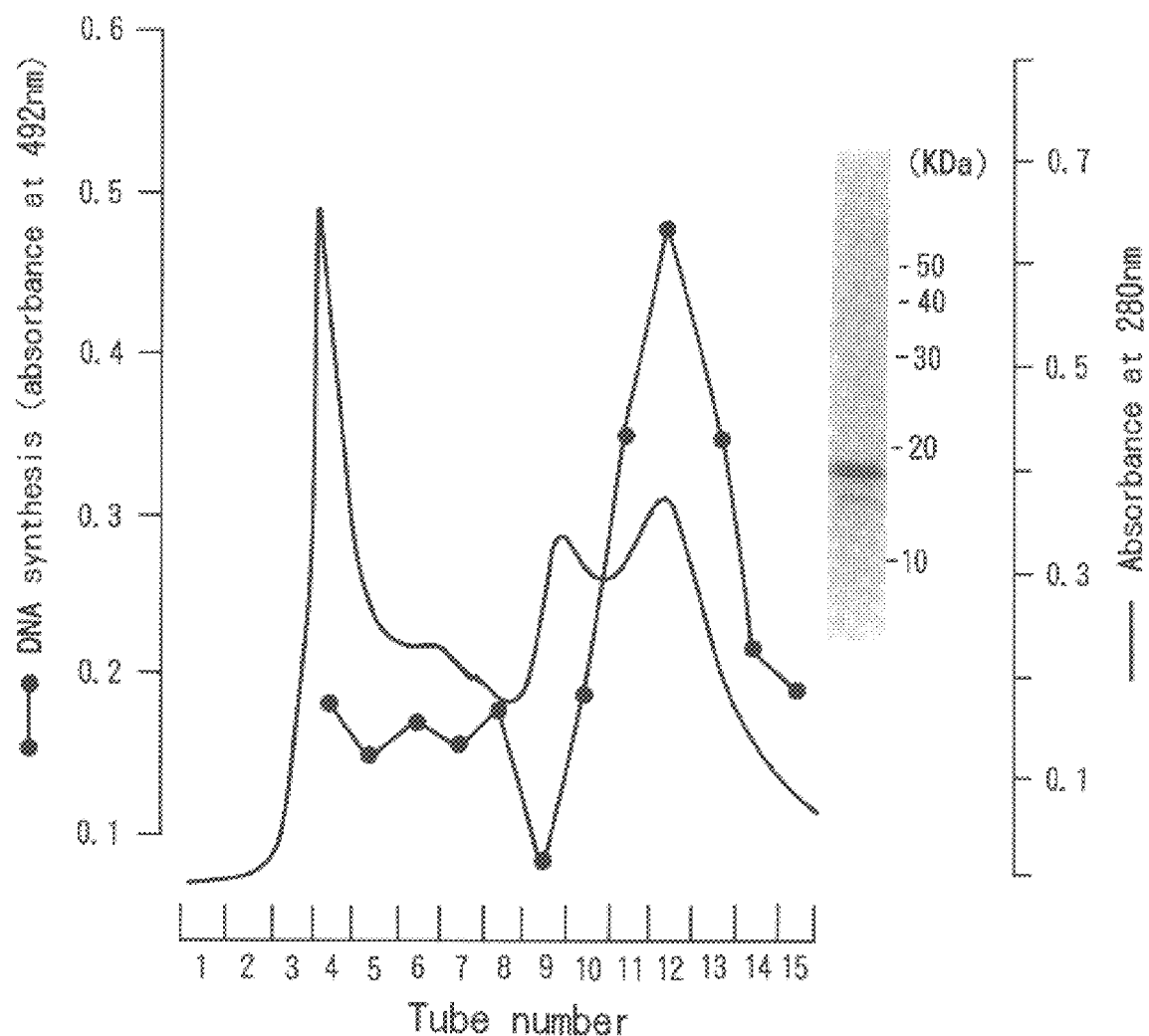
FIG. 2 shows the gel filtration chromatography of fraction II obtained by the heparin-affinity chromatography. —:Absorbance at 280 nm; •—•:hepatocytes growth promoting activity. The right space is proteins separated from tube 10 on SDS-PAGE.

Hence, the fractions II eluted 0.8 M to 1.4 M NaCl were collected from the fractions obtained from the heparin column, and were further separated by gel filtration chromatography. The column was equilibrated previously with PBS buffer and the proteins adsorbed onto the column were eluted with the same buffer. A plurality of the resulting proteins were examined for their proliferation activity on hepatocytes by using the incorporation of BrdU measured in the same manner as above, and as shown in FIG. 2, the eluates of tube 10 to 15 showing the activity were pooled, desalted, concentrated, and subjected to SDS-polyacrylamide gel electrophoresis. The result was indicated in the right space of FIG. 2. As being clear from FIG. 2, a single band between the molecular weights 10,000 and 20,000 was obtained, and from this band, one protein was purified.

By determining the amino acid sequence of this protein, it was found that 15 contiguous amino acids in its amino acid sequence agreed completely with a known amino acid sequence of mouse PTN (Biochemical and Biophysical Communications, vol. 173, No. 1, pp. 246–251, 1990), and thus this protein was confirmed to be 3T3 cell-derived PTN.

Example 2

Acquisition of Hepatocytes and Primary Culture

Hepatocytes were collected from 10-week-old Fisher rats by a collagenase perfusion method and centrifuged at low speed (50 g, 1 min.×3 times) to give a parenchymal cell fraction as precipitates. These cells were inoculated onto a culture vessel of 3.5 cm in diameter ($4 \times 10^4$ cells/vessel) and cultured at 37° C. in a 5% $CO_2$ atmosphere for 2 to 3 hours in DMEM medium (10% FBS, 44 mM $NaHCO_3$, 20 mM HEPES, 0.5 mg/l insulin, $10^{-7}$ M dexamethasone, 30 mg/l L-proline, penicillin and streptomycin). Then the culture medium was exchanged with DMEM medium prepared by adding PTN (10 ng/ml) in Example 1, 10 mM nicotinamide, 10 ng/ml EGF and 0.2 mM L-ascorbic acid phosphate to the above medium, and on Day 4 of culture, 1% DMSO was added to the medium, and culture was continued. Separately, hepatocytes were culture in the presence of commercially available human PTN (R&D Systems Inc.) in place of 3T3 cell-derived PTN or in the absence of PTN (control), and the degree of proliferation of hepatocytes was determined in terms of incorporation of BrdU.

As a result, it was confirmed that (both 3T3 cell-derived and commercially available) PTN promoted the proliferation of hepatocytes.

Figure 3:
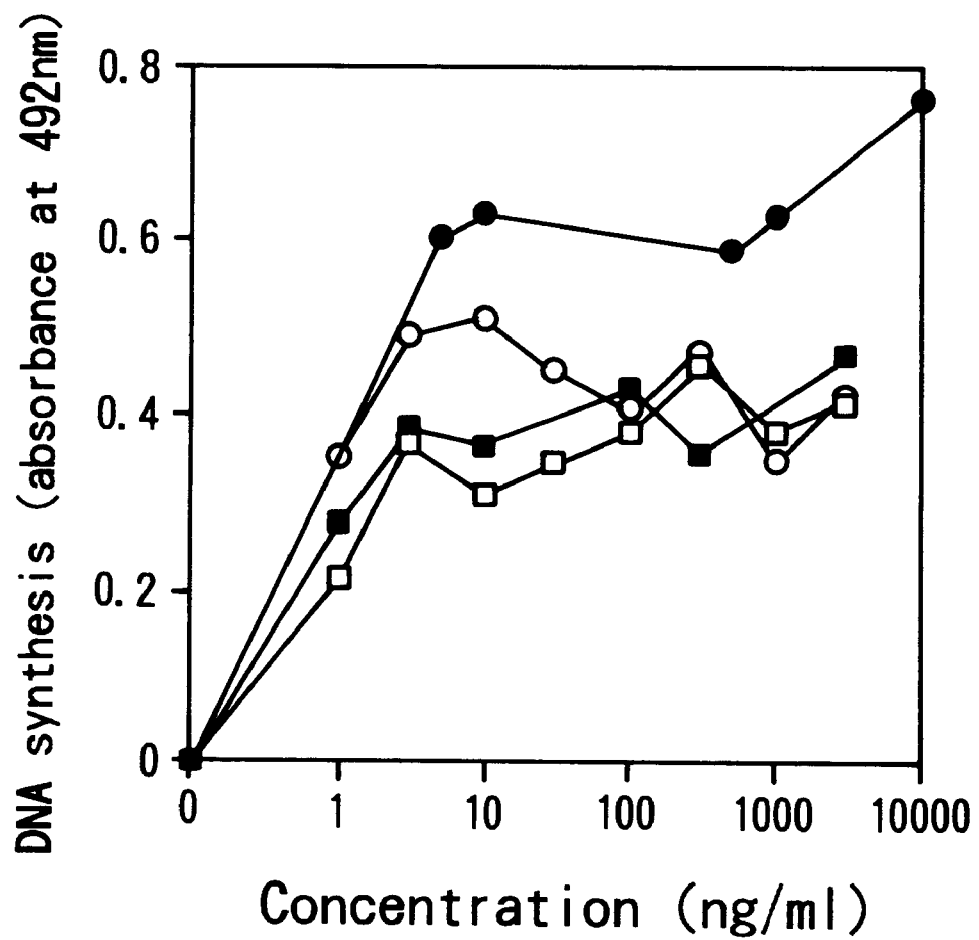
FIG. 3 shows the degree of DNA synthesis of hepatocytes by PTNs. ●:PTN purified from 3T3 cell-CM; ○:synthetic human PTN; □:recombinant human PTN; ■:synthetic human midkine.

Furthermore, DNA synthesis of hepatocytes by PTN was measured. Hepatocytes ($4 \times 10^3$ cells/$cm^2$) were cultured for 6 days in 1.6-cm wells in 0.4 ml of HCGM containing varied amounts of PTN or midkine. Media were refilled at day 4. DNA synthesis was measured by incubating the cells with BrdU for the last 2 days. The results were shown in FIG. 3. Among PTNs, the PTN purified from 3T3 cell-CM was most effective for stimulating DNA synthesis of hepatocytes.

Example 3

Subculture of Hepatocytes

In the primary culture in Example 2, the medium was removed from the vessel after hepatocyte colonies were formed, and the colonies were treated with 0.02% EDTA and 0.05% trypsin and dispersed in a solution. This cell dispersion was divided by pipetting to give dispersions of hepatocytes. Then, each dispersion was filtered through a filter with a pore diameter of 20 μm to remove small aggregations of cells therefrom, and most of the cells were thereby dispersed. These dispersed cells were plated as a thin layer onto a vessel and cultured again in DMEM medium (10% FBS, 44 mM $NaHCO_3$, 20 mM HEPES, 0.5 mg/l insulin, $10^{-7}$ M dexamethasone, 30 mg/l L-proline, penicillin and streptomycin) to which PTN prepared in Example 1 had been added, and the formation of colonies and the number of cells per colony were determined. Separately the cells were cultured in the same manner in fresh DMEM medium not containing PTN as the control, and the formation of colonies and the number of cells were determined.

The result indicated that the hepatocytes cultured in the PTN-containing medium produced more colonies than in the control and also that the number of cells per colony was significantly higher than in the control.

What is claimed is:

1. A method of forming a primary culture of hepatocytes, which comprises culturing hepatocytes isolated from the liver of a matured mammal in a cell culture medium, said cell culture medium being supplemented with pleiotrophin, fetal bovine serum, nicotinamide and ascorbic acid, to form the primary colonies of hepatocytes.

2. The method according to claim 1, wherein the medium is DMEM.

3. The method according to claim 2, wherein the DMEM cell culture medium is further supplemented with epidermal growth factor and DMSO.

4. The method according to claim 1, wherein the DMEM cell culture medium is further supplemented with epidermal growth factor and DMSO.

5. A method of forming multiple subcultures of hepatocytes, which comprises:

(a) culturing hepatocytes isolated from the liver of a matured mammal in a cell culture medium, said cell culture medium being supplemented with fetal bovine serum, nicotinamide and ascorbic acid, to form primary colonies of hepatocytes;

(b) detaching the colonized hepatocytes from the cell culture medium by using an EDTA/trypsin solution to disperse the hepatocytes;

(c) re-culturing the dispersed hepatocytes in another cell culture medium supplemented with pleiotrophin, fetal bovine serum, nicotinamide and ascorbic acid, to form the subculture colonies of hepatocytes; and (d) repeating steps (b) and (c) to form multiple subculture colonies of hepatocytes.

6. The method according to claim 5, wherein the cell culture medium is DMEM.

7. The method according to claim 6, wherein the DMEM cell culture medium is further supplemented with epidermal growth factor and DMSO.

8. The method according to claim 5, wherein the DMEM cell culture medium is further supplemented with epidermal growth factor and DMSO.

9. A method of forming multiple subcultures of hepatocytes, which comprises:

(a) culturing hepatocytes isolated from the liver of a matured mammal in a cell culture medium, said cell culture medium being supplemented with pleiotrophin, fetal bovine serum, nicotinamide and ascorbic acid, to form primary colonies of hepatocytes;

(b) detaching the colonized hepatocytes from the cell culture medium by using a solution containing EDTA and trypsin to disperse the hepatocytes;

(c) re-culturing the dispersed hepatocytes in another cell culture medium supplemented with pleiotrophin, fetal bovine serum, nicotinamide and ascorbic acid, to form subculture colonies of hepatocytes; and (d) repeating steps (b) and (c) to form multiple subculture colonies of hepatocytes.

10. The method according to claim 9, wherein the cell culture medium is DMEM.

11. The method according to claim 10, wherein the DMEM cell culture medium is further supplemented with epidermal growth factor and DMSO.

12. The method according to claim 9, wherein the DMEM cell culture medium is further supplemented with epidermal growth factor and DMSO.

13. A method of forming a subculture of hepatocytes, which comprises:

(a) culturing hepatocytes isolated from the liver of a matured mammal in a cell culture medium, said cell culture medium being supplemented with fetal bovine serum, nicotinamide and ascorbic acid, to form primary colonies of hepatocytes;

(b) detaching the colonized hepatocytes from the cell culture medium by using an EDTA/trypsin solution to disperse the hepatocytes;

(c) re-culturing the dispersed hepatocytes in another cell culture medium supplemented with pleiotrophin, fetal bovine serum, nicotinamide and ascorbic acid, to form the subculture colonies of hepatocytes.

14. The method according to claim 13, wherein the cell culture medium is DMEM.

15. The method according to claim 14, wherein the DMEM cell culture medium is further supplemented with epidermal growth factor and DMSO.

16. The method according to claim 13, wherein the DMEM cell culture medium is further supplemented with epidermal growth factor and DMSO.

17. A method of forming a subculture of hepatocytes, which comprises:

(a) culturing hepatocytes isolated from the liver of a matured mammal in a cell culture medium, said cell culture medium being supplemented with pleiotrophin, fetal bovine serum, nicotinamide and ascorbic acid, to form primary colonies of hepatocytes;

(b) detaching the colonized hepatocytes from the cell culture medium by using a solution containing EDTA and trypsin to disperse the hepatocytes;

(c) re-culturing the dispersed hepatocytes in another cell culture medium supplemented with pleiotrophin, fetal bovine serum, nicotinamide and ascorbic acid, to form subculture colonies of hepatocytes.

18. The method according to claim 17, wherein the cell culture medium is DMEM.

19. The method according to claim 18, wherein the DMEM cell culture medium is further supplemented with epidermal growth factor and DMSO.

20. The method according to claim 17, wherein the DMEM cell culture medium is further supplemented with epidermal growth factor and DMSO.

* * * * *